United States Patent
Fauchon et al.

(10) Patent No.: US 10,946,213 B2
(45) Date of Patent: Mar. 16, 2021

(54) INFRARED RADIATION DEVICE

(71) Applicant: VITAL TECH, Paris (FR)

(72) Inventors: Eric Fauchon, Boulogne Billancourt (FR); Alexandra Gavsevitch, Boulogne Billancourt (FR)

(73) Assignee: VITAL TECH, Paris (FR)

( * ) Notice: Subject to any disclaimer, the term of this patent is extended or adjusted under 35 U.S.C. 154(b) by 785 days.

(21) Appl. No.: 15/031,599

(22) PCT Filed: Oct. 27, 2014

(86) PCT No.: PCT/EP2014/073032
§ 371 (c)(1),
(2) Date: Apr. 22, 2016

(87) PCT Pub. No.: WO2015/059313
PCT Pub. Date: Apr. 30, 2015

(65) Prior Publication Data
US 2016/0250499 A1    Sep. 1, 2016

(30) Foreign Application Priority Data
Oct. 25, 2013    (FR) ...................................... 1360481

(51) Int. Cl.
*A61N 5/06* (2006.01)
*A61F 7/00* (2006.01)

(52) U.S. Cl.
CPC .............. *A61N 5/0625* (2013.01); *A61F 7/00* (2013.01); *A61F 2007/0088* (2013.01);
(Continued)

(58) Field of Classification Search
CPC combination set(s) only.
See application file for complete search history.

(56) References Cited

U.S. PATENT DOCUMENTS

| 6,004,344 A | 12/1999 | Fujii |
| 6,896,693 B2 * | 5/2005 | Sullivan ............... A61N 5/0616 606/10 |

(Continued)

FOREIGN PATENT DOCUMENTS

| CA | 2 450 633 | 3/2004 |
| GB | 2 258 474 | 2/1993 |
| WO | WO-9519810 A1 * | 7/1995 ............... A61N 5/06 |

*Primary Examiner* — Kaitlyn E Smith
(74) *Attorney, Agent, or Firm* — Hauptman Ham, LLP (57) ABSTRACT

The present invention relates to an infrared radiation device including a mounting (2) capable of receiving a user (9) and a covering portion (1) capable of covering the user (9), the covering portion (1) including at least one heating layer (5a, 5b, 5c) capable of emitting infrared radiation (6) in a predetermined range of wavelengths towards at least one portion of the space located between the inner surface of the heating layer (5a, 5b, 5c) and the mounting (2), the device being characterised in that said heating layer (5a, 5h, 5c) is adjusted by at least one controller (10) including power-supply means (16) supplying the power necessary for infrared emission and at least one programmer (15) determining the parameters of a radiation session, by defining pulsations that control at least one synchronous static relay (14) which supplies said heating layer (5a, 5b, 5c) with the power provided by the power-supply means (16) during the pulsations.

20 Claims, 5 Drawing Sheets

(52) U.S. Cl.
CPC ............... *A61F 2007/0093* (2013.01); *A61F 2007/0096* (2013.01); *A61N 2005/0626* (2013.01); *A61N 2005/0637* (2013.01); *A61N 2005/0638* (2013.01); *A61N 2005/0659* (2013.01); *A61N 2005/0666* (2013.01)

(56) References Cited

U.S. PATENT DOCUMENTS

| | | | | |
|---|---|---|---|---|
| 8,690,933 | B2* | 4/2014 | Mitchell | A61N 5/0618 128/898 |
| 9,265,690 | B2* | 2/2016 | Kriksunov | A61F 7/007 |
| 9,795,502 | B1* | 10/2017 | Kopes | A61F 7/007 |
| 9,808,644 | B2* | 11/2017 | Daffer | A61N 5/0613 |
| 2002/0026226 | A1* | 2/2002 | Ein | A61F 7/007 607/108 |
| 2002/0115946 | A1* | 8/2002 | Cutler | A61H 23/0263 601/57 |
| 2002/0183814 | A1 | 12/2002 | Ono | |
| 2006/0136020 | A1 | 6/2006 | Dissault | |
| 2006/0226378 | A1 | 10/2006 | Yabiku | |
| 2007/0219605 | A1* | 9/2007 | Yaroslavsky | A61N 5/0613 607/100 |
| 2007/0233208 | A1* | 10/2007 | Kurtz | A61N 5/0613 607/88 |
| 2009/0107984 | A1* | 4/2009 | Kohn | A61F 7/007 219/528 |
| 2009/0222070 | A1* | 9/2009 | Daffer | A61N 5/0613 607/91 |
| 2010/0004715 | A1* | 1/2010 | Fahey | A61H 39/002 607/48 |
| 2010/0106229 | A1* | 4/2010 | Gammons | A61F 7/0085 607/104 |
| 2011/0054573 | A1* | 3/2011 | Mitchell | A61N 5/0618 607/90 |
| 2011/0144727 | A1* | 6/2011 | Benedict | A61N 5/0613 607/91 |
| 2013/0096595 | A1* | 4/2013 | Myhr | A61N 1/403 606/169 |
| 2015/0265458 | A1* | 9/2015 | Andersen et al. | A61F 7/007 607/113 |
| 2017/0216087 | A1* | 8/2017 | Srinivasan | A61F 7/007 |
| 2018/0043176 | A1* | 2/2018 | Daffer | A61N 5/0613 |

* cited by examiner

INFRARED RADIATION DEVICE

TECHNICAL FIELD OF THE INVENTION

The present invention relates to the field of radiation treatments, more particularly an infrared irradiation device.

TECHNOLOGICAL BACKGROUND OF THE INVENTION

Infratherapy or the use of infrared waves in therapy allows resonance of muscular tissue, boosting cellular functions and improving blood circulation, the cardiovascular system as well as the immune system. The radiant energy of an infrared irradiation device functions by resonance frequency on the cellular membrane and produces detoxification in depth of the upper layers of the human body subjected to various contaminants. For example, this radiant energy can have a beneficial effect on wellbeing, on health or on sporting performance of a user (9) of an infrared irradiation device.

Infrared irradiation devices are known from the prior art, comprising a support intended to receive a user and a covering part specifically for covering the user and comprising a heating layer including infrared emission means for irradiating the user. Some of these devices often have infrared emission means comprising carbon plates which are reliable and supply radiation in advantageous wavelengths. However, these devices generally have the disadvantage of not guaranteeing durability and/or reliability of the device. In particular, devices intended for professional use need to be able operate often and for a long time. It is particularly important to ensure good reliability of the device over time.

GENERAL DESCRIPTION OF THE INVENTION

The aim of the present invention is to provide an infrared irradiation system improving durability and/or the reliability of the device. In particular, the invention regulates temperature and ensures optimal operation over time, during each session and/or during the optimised life period of the device.

To this purpose, the invention relates to an infrared irradiation device comprising a support capable of receiving a user and a covering part capable of covering the user, the covering part comprising at least one heating layer capable of emitting infrared radiation in a determined range of wavelengths to at least one part of the volume located between the inner face of the heating layer and the support, the device being characterized in that said heating layer is regulated by at least one controller comprising power-supply means providing the power necessary for emission of infrared and at least one programmer determining the parameters of an irradiation session, by defining time slots during the session, these time slots controlling at least one synchronous static relay or another type of contactor which delivers to said heating layer the power provided by the power-supply means during the time slots.

According to another particular feature, said synchronous static relay delivers no current to said heating layer beyond the time slots defined by the programmer.

According to another particular feature, the programmer calculates the time at which the time slots must be delivered, and their period, as a function of the quantity of energy to be provided, and therefore of the requested temperature.

According to another particular feature, the programmer comprises a memory storing a plurality of predefined programs corresponding to various types of irradiation sessions and defining the period of the irradiation session and/or the temperature(s) to be reached during the session.

According to another particular feature, the programmer calculates the time slots as a function of temperature information originating from at least one probe or sensor of the device.

According to another particular feature, said at least one probe or sensor is at least one temperature probe allowing the programmer adjust the pulses as a function of the temperature obtained in the device.

According to another particular feature, the device is fitted with electrical safety means to protect the user from any problems in the electrical circuits of the device.

According to another particular feature, the covering part further comprises a reflective layer of infrared radiation.

According to another particular feature, the support comprises a second heating layer capable of emitting radiation in at least one part of the volume between the inner face of the first heating layer and the support.

According to another particular feature, an end, according to the longitudinal axis, of the covering part comprises a third heating layer closing the covering part.

According to another particular feature, the covering part comprises at least two portions, the second portion of the covering part being capable of sliding relative to the first portion parallel to the longitudinal axis so as to retract in or on the first portion.

According to another particular feature, the power cabling of the first heating layer comprises a guide to allow sliding of the two portions without jamming and/or damaging the cabling.

According to another particular feature, the covering part comprises an outer layer protecting the interior of the covering part.

According to another particular feature, the heating layers comprise at least one carbon plate.

According to another particular feature, the reflective layer comprises at least one layer made of aluminium.

According to another particular feature, the outer layer is made of wood.

According to another particular feature, the support is made of wood.

According to another particular feature, the inner surface of the covering part is covered in textile.

According to another particular feature, the irradiation device comprises a lifting system of the covering part, the first portion or the second portion of the covering part being fixed on at least the lifting system of the covering part, the lifting system of the covering part comprising at least one thrust jack whereof an end is fixed on the support or on the feet of the support and the other end is fixed on the first or the second portion of the covering part such that the jack can exert thrust tending to lift an end of the covering part, the other end of the covering part being fixed on the support by means of a hinge allowing the longitudinal axis of the covering part to form a non-zero angle with the plane of the support.

According to another particular feature, the power cabling of the heating layer passes near the hinge of the covering part to make for easier pivoting without jamming and/or damaging the cabling.

The invention, with its characteristics and advantages, will emerge more clearly from the description given in reference to the appended drawings, in which.

DESCRIPTION OF PREFERRED EMBODIMENTS OF THE INVENTION

The rest of the description will make reference to the figures cited hereinabove.

The invention relates to an infrared irradiation device. This device is sometimes also called an individual sauna. In the rest of the description, the device could be called irradiation device or simply device.

In differing from a traditional sauna which heats a body indirectly by heating ambient air, the infrared irradiation device heats the body directly by heat produced by infrared radiation (6). The temperature reached by the device can advantageously be in a range varying from ambient temperature to around 80° C., but can extend to temperatures reached by traditional saunas as high as 105° C. The ambient temperature is generally a temperature equal to 20° C. or slightly less than 20° C., but ambient temperature can go to 35° C. or 40° C. The fact of regulating the temperature below excessive values advantageously improves the lifetime of the device, apart from the comfort of the patient.

Also, the irradiation device comprises infrared emission means (5a, 5b, 5c) which are preferably formed by carbon plates and which are fed, via the sector, to emit infrared in a determined range of wavelength. These infrared emission means are regulated by a controller (10) comprising power-supply means (16) providing the power necessary for emission of infrared and a programmer (15) determining the parameters of an irradiation session, by defining time slots (pulsations or pulses) during the session, these time slots controlling at least one synchronous static relay or another type of contactor delivering, by means of infrared emission means (5a, 5b, 5c), the power provided by the power-supply means (16) during the time slots. In some preferred embodiments, the contactor is a synchronous static relay (14) which delivers no current to the infrared emission means (5a, 5b, 5c) beyond the time slots defined by the programmer (15).

The programmer (15) defines various parameters relative to the control of infrared emission means (5a, 5b, 5c) during at least one irradiation session. The programmer (15) preferably calculates the time at which the time slots must be delivered during the session, and their period, as a function of the quantity of energy to be provided, and therefore of the requested temperature. This temperature is generally determined as a function of the wavelength provided for the emission means and as a function of the physical parameters of the device (dimensions, insulation etc.). Also, this programmer can store in memory a plurality of predefined programs corresponding to various types of irradiation sessions. These programs define parameters of the session, for example such as the period of the irradiation session, the temperature(s) to be reached during the session and can take into account other information such as for example the size, the weight or the age of the user to be irradiated, the ambient temperature of the room and/or the temperature inside the device. In this way, during an irradiation session the controller (10) feeds the infrared emission means (5a, 5b, 5c) for at least one period of time determined by the programmer (15), or several periods of irradiation time if the program provides pauses during the session. During each period of irradiation time, the programmer (15) delivers a plurality of pulsations (pulses) by way of the time slots defined in the program(s) to control the infrared emission means (5a, 5b, 5c). These time slots have a determined period and recurrence to optimise regulation of the irradiation and reliably produce the temperature defined in the program(s). In fact, in proceeding with pulsations instead of heating continuously during a given period of irradiation time, the irradiation is best controlled at the infrared emission means (5a, 5b, 5c) which are more capable of providing the preferred temperature, whereas with continuous feed they would heat too much or too little and too fast or too slowly (according to electrical power and the supply period provided). The infrared irradiation devices of the prior art are known to have such problems since they include just one timer defining a period of irradiation time during which the infrared emission means (5a, 5b, 5c) are fed non-stop. Inversely, the pulsed current obtained by the controller (10) regulates at variable frequencies (according to the period of pulses, for example of the order of Hz to kHz), the feed of the infrared emission means (5a, 5b, 5c) and accordingly attains very fine control of the temperature provided.

In some embodiments, the programmer (15) calculates the pulses as a function of temperature information originating from at least one probe (18) of the device. In this way, the device is fitted with one or more temperature probes (18, 18a, 18b, 18c) allowing the programmer adjust the pulses as a function of the temperature obtained in the device. Other types of probes or sensors can be used (preferably as a complement to the temperature probes), such as for example weight sensors letting the programmer adjust the pulses automatically or adjust the type of predefined programme to be used as a function of the weight of the user. The programmer can also use hydrometry probes to refine regulation.

This arrangement has the advantage of feeding the infrared emission means only when necessary (during pulses defined by the programmer) and allowing fine temperature regulation. In some preferred embodiments, by way of the programmer(s) (15) defining the pulses and by way of the synchronous static relay(s) (14) which cut the power to zero voltage beyond the pulses, the infrared emission means (5a, 5b, 5c) are stressed only when necessary, which improves the durability of the device and in particular of the infrared emission means (preferably formed by carbon plates). Other types of contactors can be used, but synchronous static relays are preferred to preserve the infrared emission means. Also, these infrared emission means are stressed by the programmer to reach and maintain a defined temperature and fine regulation obtained by the pulsations of the programmer improves the reliability of the device as detailed hereinabove. Finally, the synchronous static relays which spare the infrared emission means by the fact that they cut voltage to 0 in the absence of pulse of the programmer, also have the advantages of limiting perturbations, producing fewer parasites and radiating emissions, which can be particularly advantageous, especially if the frequency of the pulses (determined by the programmer) is high. These advantages also prolong the lifetime of the device in its entirety.

Figure 1:
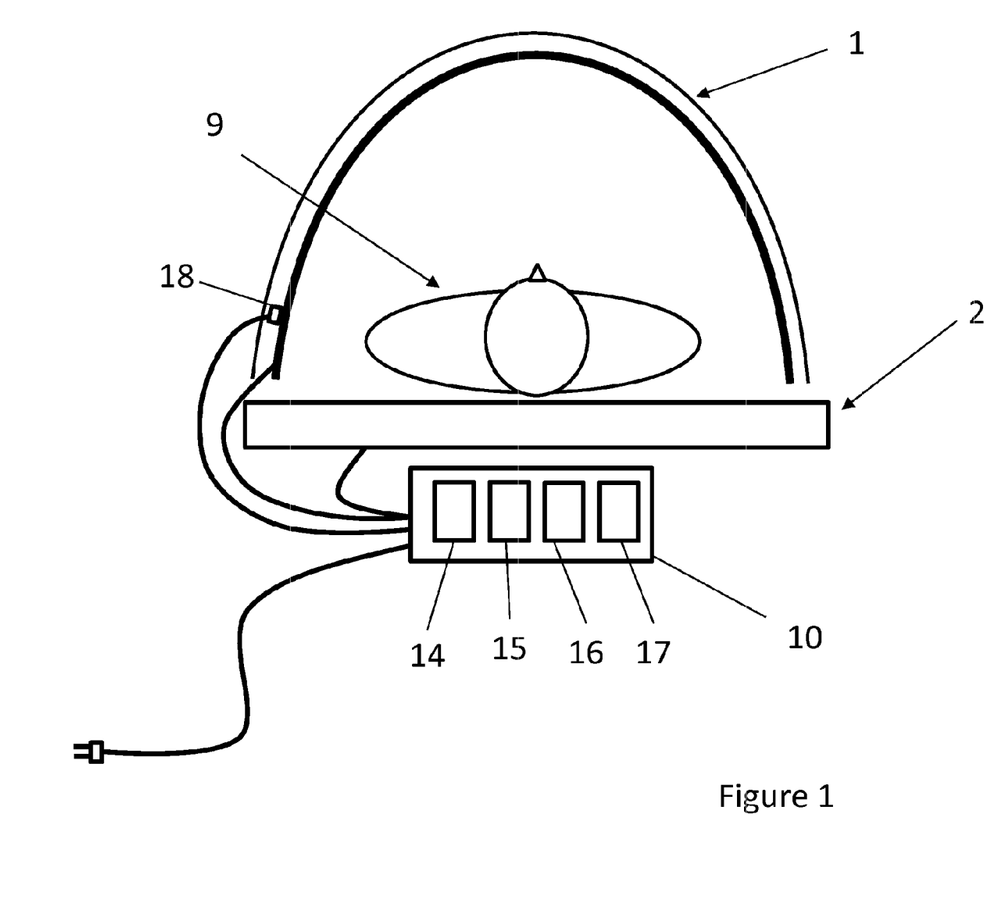
FIG. 1 illustrates a view of the device according to a viewing axis parallel to the longitudinal axis of the device.
Figure 2:
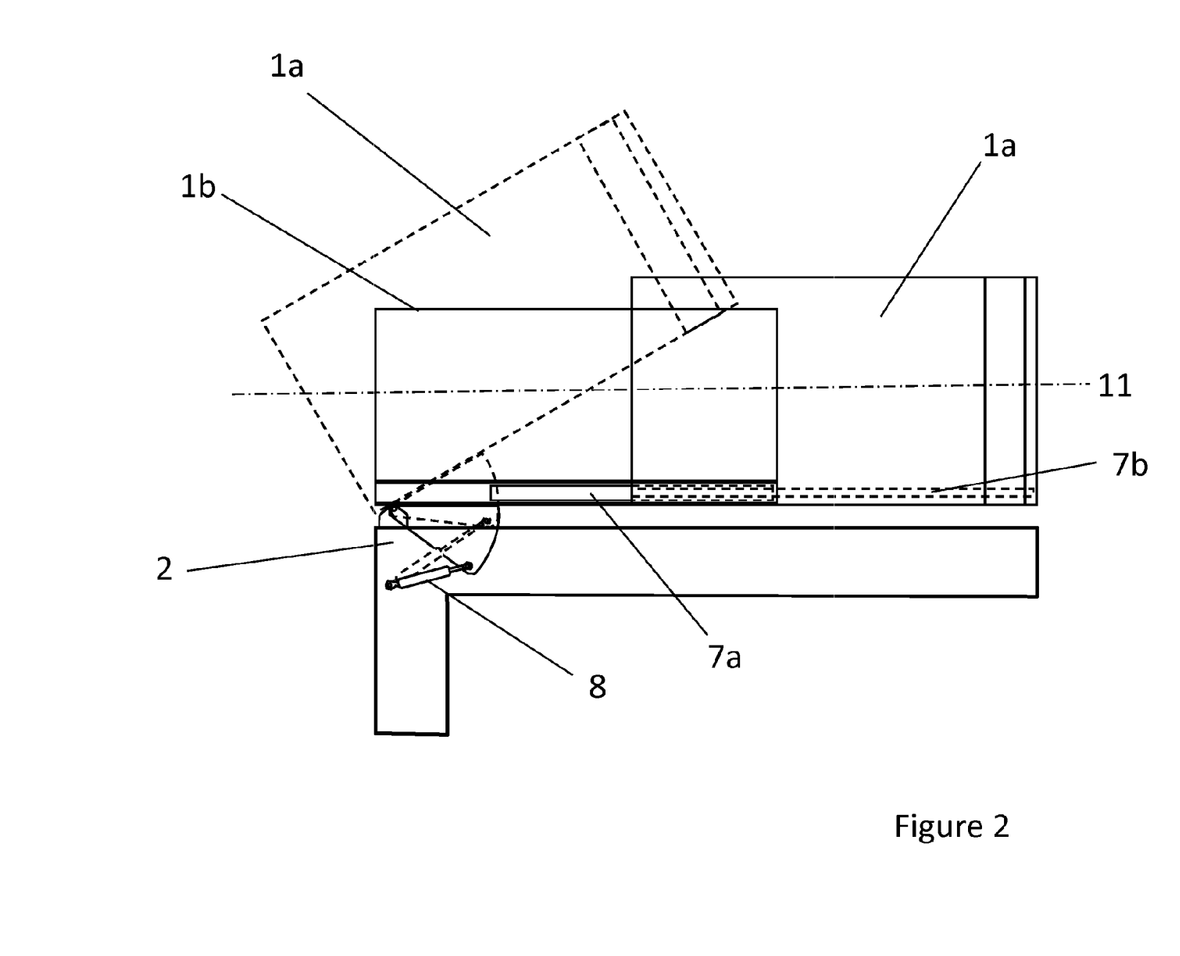
FIG. 2 illustrates a profile view of the device according to two positions of the covering part.
Figure 3:
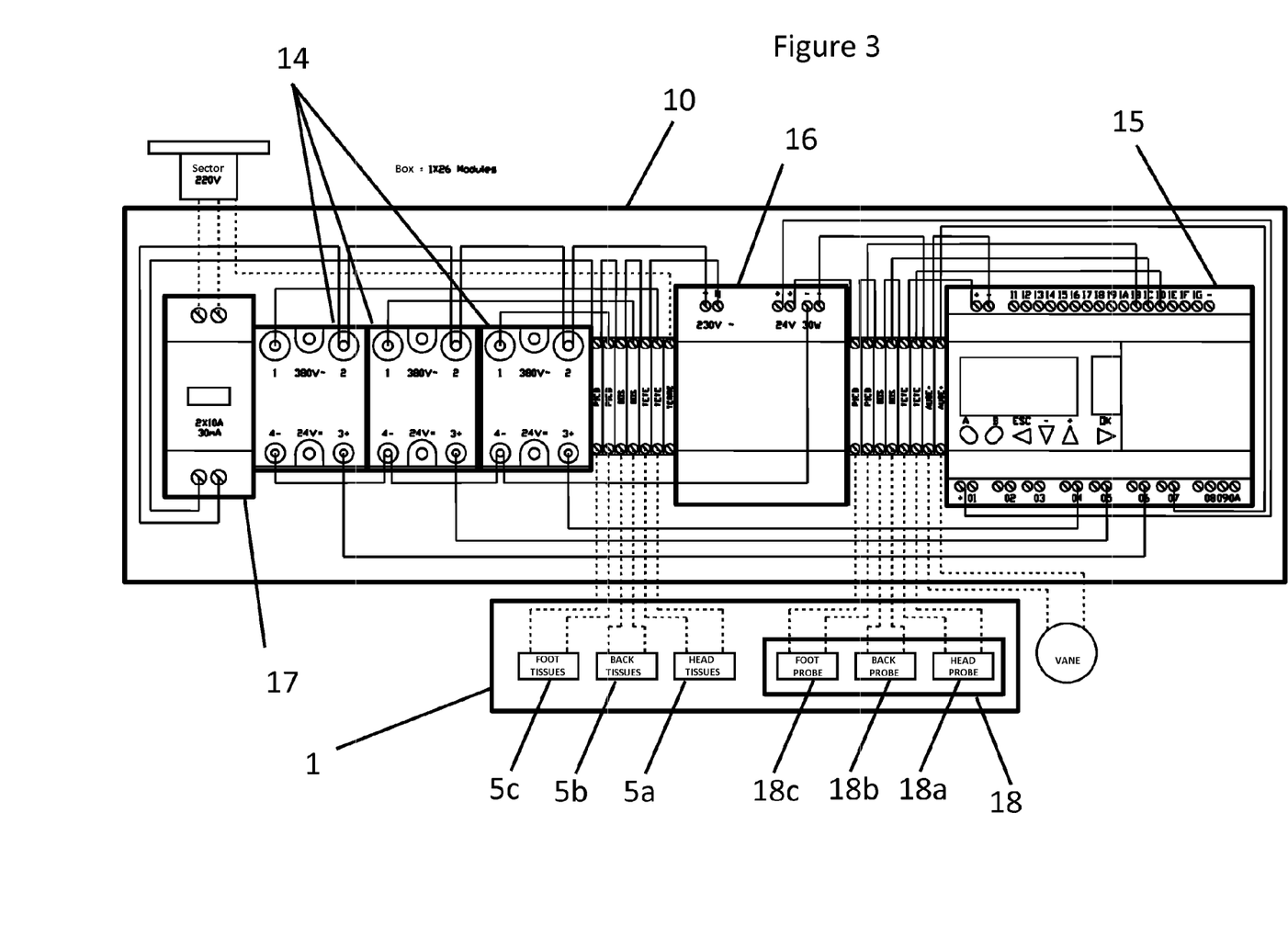
FIG. 3 illustrates a cabling drawing of the device with its controller.
Figure 4:
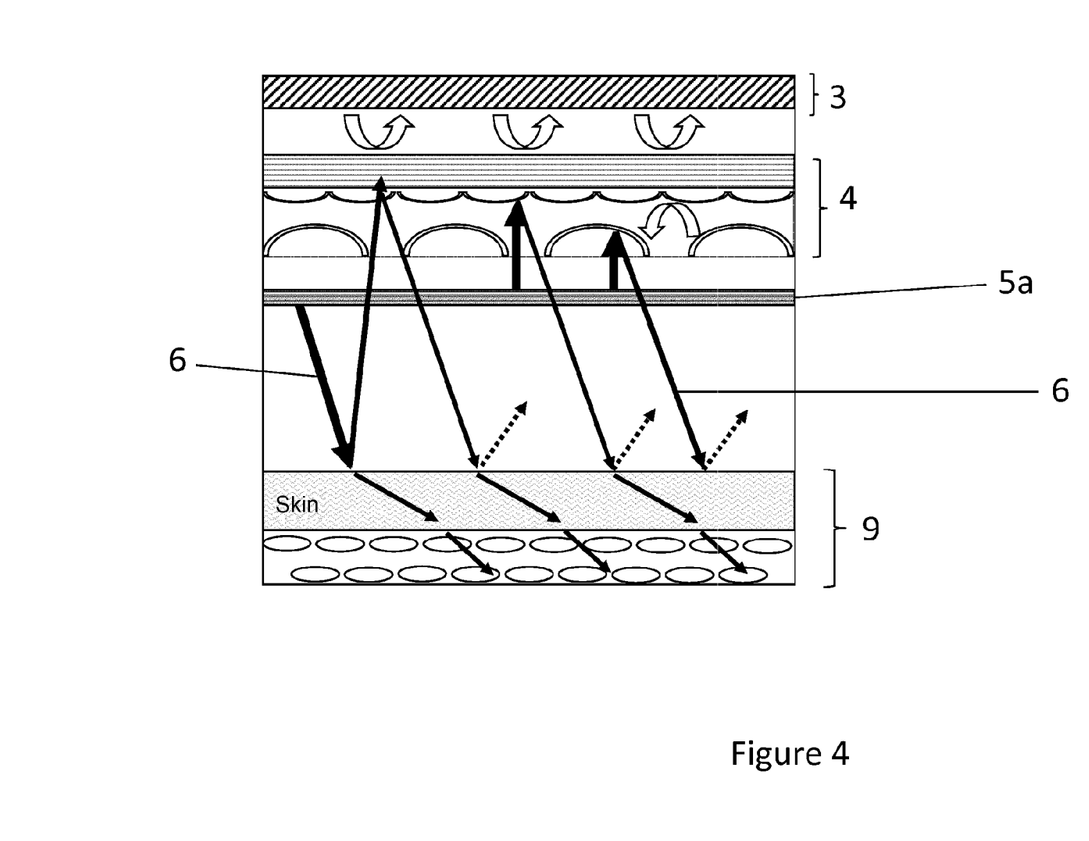
FIG. 4 illustrates schematically the performance of infrared radiation between the covering part and the user of the device.

Electrical safety means (17) are provided in general, such as for example a differential circuit breaker (17), to protect the user from any problems in the electrical circuits of the device, such as for example shown in FIG. 3.

FIG. 3 illustratively and non-limiting shows a cabling drawing of a device according to preferred embodiments of the invention. The sector delivers an alternating current to a transformer (16) capable of providing power to the infrared emission means. This transformer feeds (in 24V in the example shown) at least one programmer (15) which controls (by current pulses, at 24V in the example shown) at least one synchronous static relay (14). During the pulses the synchronous static relay delivers to the infrared emission means the power allowing the infrared emission necessary to reach the defined temperature. In the absence of pulse it cuts the voltage to a zero value and the infrared emission means are then protected and no emission of perturbations, parasites or radiating emissions can shorten the lifetime of the device.

In some embodiments, the device comprises regulating means for adjusting the intensity of radiation of the infrared emission means. These regulating means control the controller. This command varies naturally as a function of the selected embodiments and it is understood that one can, for example, either simply to define a temperature or to select a given programme, or to input a set of information necessary for calculations of the pulses by the programmer.

The illustrative and non-limiting example of FIG. 3 illustrates 3 synchronous static relays (14) which feed 3 pairs of infrared emission means (designated by the term "tissues" in FIG. 3), which corresponds in fact to the illustrative and non-limiting arrangements of the device shown in the other figures. Similarly, 3 pairs of probes (18a, 18b, 18c) are shown to provide the programmer with the temperatures measured in the portions of the device which correspond to each pair of emission means. It is evident that it is possible to move away from this example and remain within the scope of the invention, for example by providing fewer probes than there are emission means. Also, it is of course understood that these numbers could vary, but that preferably as many relays are provided as there will be emission means to be controlled independently. Similarly, only one transformer (16), one programmer (15) and one circuit breaker (17) are illustrated but if the device exceeded the capacities of each of these components they would be multiplied to obtain the same results.

In the rest of the description given in reference to the figures, the infrared emission means are designated by the terms of heating layer or carbon plate.

The infrared irradiation device comprises a support (2). This support (2) receives a user (9), for example, lying down. The support (2) is surmounted of the covering part (1) which covers and borders the sides of the user (9) who is for example lying down on the support (2). The support (2) and the covering part (1) are arranged according to a longitudinal axis of the device.

The covering part (1) comprises at least one heating layer. In some embodiments, this layer comprises at least one carbon plate. In the present description the heating layers are designated therefore sometimes, non-limiting, by the term "carbon plates". The carbon plates are generally produced from superconducting polymer tissue composed of carbon, silica and graphite. The tissue is preferably insulated between two epoxy laminated fiberglass sheets and rolled at high temperature. The strong density and regular distribution of carbon allow regular emission of the infrared radiation (6) over its entire surface. A fiberglass sheet generally comprises on two edges opposite the carbon plate, material conducting electricity such as copper in contact with the tissue and fed by electricity by means of a controller (10). For example, the two edges have two copper strips feeding the tissue.

The covering part (1) comprises at least one heating layer (5a, 5b). This heating layer (5a, 5b) is capable of emitting infrared radiation (6) in at least one part of the volume located between the inner face of the heating layer (5a, 5b) and the support (2).

A particular feature of the infrared radiation (6) is emission of waves of the first heating layer (5a) which causes a rise in temperature of the user (9) receiving the waves emitted.

In a non-limiting way, the waves emitted have wavelengths comprised between 0.76 μm and 10 μm. The advantage of this heating mode is that infrareds are not or poorly absorbed by air, while solids and liquids absorb them easily. The wavelengths are inversely proportional to the temperature of their emitter. According to Wien's law, the higher the temperature of the emitter, the shorter the wavelength.

Absorption by the biological tissues of photons of infrared waves modifies the state of vibration or molecular rotation. Due to their low energy, infrared photons cannot produce ionisation, or photochemical reactions. Infrared radiation is overall seen as a heat source producing relaxation and wellbeing, or even added advantages as described in the present application.

In some embodiments, the heating layers of the device emit long infrared radiation (6) in the wavelength range comprised between 6 μm to 19 μm. The human skin is complex material considered as a grey body whereof the emissivity is close to that of a black body. It dissipates its heat partly by radiation. For a black body, the Stefan-Boltzmann law integrates the notion of emissivity which illustrates a link between the energy radiated by a surface undergoing an incident flow and the energy which a black body would radiate at the same temperature. Emissivity can vary as a function of wavelength. Wien's displacement law is obtained by derivation of Planck's law. It gives the wavelength corresponding to the maximum spectral radiation of a black body as a function of its temperature. From this law, it is seen that at a temperature of 35° C. the skin emits maximum energy at a wavelength of 9.4 μm. At a temperature of 37° C., the skin emits maximum energy at a wavelength of 9.3 μm. At a temperature of 38.4° C., the skin emits maximum energy at a wavelength of 9.3 μm.

Consequently, the heating layers of the infrared irradiation device preferably emit at a length of between 8.7 μm and 9.5 μm. More preferably, they emit at a wavelength of 9.3 μm.

Also, it is known that some bodies, especially comprising carbon and silicon can emit infrared radiation which spreads in a preferred direction perpendicular to its surface, for example as is demonstrated in the doctorate thesis of Martine Laroche, (*Role of surface waves in the modification of radiative properties of microstructured materials. Application to designing infrared sources and to the thermophotovoltaic effect.* École centrale, Paris, 2005). So, the heating layer(s), preferably comprising carbon, silicon and graphite, utilised in some embodiments of the present application, emit infrared radiation whereof the preferred direction is perpendicular to their surface at all points. This directional radiation can be felt by the fact that the heating layer(s) heat the space facing it and not to the side. The advantage of this is to heat only the space inside the device and limit ambient heating in the room where the device is located. Also, various embodiments take advantage of this directional radiation by using a particular profile.

In fact, in some embodiments, the section of the first heating layer (5a) transversal to the longitudinal axis advantageously follows a form representative of a parabolic curve. Here this form of the transversal section is designated by the term profile and parabolic profile in particular. Also, as the device can comprise several heating layers, this heating layer with parabolic profile is designated here by the term "first heating layer" but this term must not be interpreted as limited as it in fact designates the radiating part of the dome above the user and is composed of one or more heating layers. The parabolic profile of the first heating layer (5a, 5b) produces a convergence area of the infrared radiation (6) best distributed over the entire body of the user (9). For example, as shown in FIG. 3, infrared radiation is emitted according to a preferred direction perpendicular to the surface of the heating layer at each point of the heating layer. The combination of the parabolic profile with this preferred perpendicular direction enables homogeneous distribution of the radiation. In the convergence area, the temperature value generated in Kelvin can be multiplied by a factor of 1.4 for two beams which cross.

In some embodiments, even though they are not preferred, the first heating layer (5a, 5b) can have a profile of half-circular form, but the infrared radiation (6) of the convergence area reduces at a single point which would be the centre of the circle of the half-circular form. The consequence of this is poorer distribution of the infrared radiation (6) which is focused on an axis parallel to the longitudinal axis of the device, while with a parabolic profile the distribution can advantageously be adjusted to at least approximately follow the outer form of the body of the user present inside the device. In this way, apart from the comfort of the user, such heat distribution allows the device to find applications in phlebology such as for example reduction in varicose veins, which would be unlikely for a device of the prior art.

In some embodiments, the function of the parabolic curve is $y=x^2-x-1$. It is evident that the golden ratio $$\frac{1+\sqrt{5}}{2}$$

is the positive solution for $x^2-x-1=0$, where x illustrates the coordinates according to the axis of the abscissae parallel to the support (2) of the device and y illustrates the coordinates according to the axis of the ordinates perpendicular to the support (2) of the device with the axis of the ordinates directed downwards.

In some embodiments, for example at the level of the controller (10), the device comprises at least one display means for displaying the wavelength emitted by the heating layer fed by means of the controller (10). Such a display can also be produced on display means (13) of the device. In fact, in some embodiments, the device comprises display means (13) for displaying information on the operation of the device, such as the temperature produced by the heating layers, the time of use of the device or other useful parameters for operating the device.

In some embodiments, the covering part (1) of the infrared irradiation device also comprises a reflective layer (4) of infrared radiation (6) on the outer face of the heating layer. The profile of the reflective layer (4) preferably follows the profile of the heating layer (5a, 5b). This reflective layer (4) reflects infrared radiation (6) which has not been absorbed by the body of the user (9) to be sent back to the body of the user (9). This allows energy-saving necessary for emitting the infrared radiation (6). This also allows safety from the infrared irradiation device, as the outer surface of the covering part (1) stays cold.

In a configuration, the reflective layer (4) comprises at least one film or a plate made of aluminium. In addition or as an alternative, it can also comprise at least one film or a plate containing cobalt, particularly effective for reflecting infrared.

In some configurations of the reflective layer (4) it comprises several components. In a preferred configuration, the components comprise six reflective films, two layers of cotton wool and six layers of foam.

In some embodiments, the covering part (1) of the device comprises an outer layer (3) protecting the interior of the covering part (1). In some preferred embodiments, this layer (3) is rigid. In some embodiments, this outer layer (3) is made of plastic material or metal, or is made of wood. In some embodiments, the outer layer (3) can be made of fiberglass or carbon fibers or any moldable fiber. In some embodiments, the outer layer (3) can be made by a combination of materials mentioned above.

The reflective layer (4) of the device is arranged between the outer layer (3) and the heating layer. The heating layer therefore has no contact with the outer layer (3) of the device, which considerably limits energy transfers by conduction and produces good thermal efficacy relative to the prior art.

In some embodiments, the outer layer (3) has a profile of parabolic form which follows the profile of the heating layer. For example, the reflective layer (4), the outer layer (3) and the first heating layer (5a) are fixed relative to each other. They are preferably fixed by fastening means supporting heat and do not cause emission of vapors, or even insulation between at least 2 of these 3 layers, for example by way of a space (e.g., an air gap) between at least 2 of these layers, in particular between the reflective layer (4) and the outer layer (3). The fastening means are for example grooves in which are nested the ends of the different layers. These grooves are arranged for example on at least two edges located at the opposite ends of the outer layer and in which the heating and reflective layers are inserted.

In some embodiments, the support (2) comprises a second heating layer (not shown) capable of emitting radiation in at least one part of the volume between the inner face of the heating layer and the support (2). For example, the second heating layer is integrated into a mattress, for example made of damping or comfortable material, placed on the support (2).

In some embodiments, a first end of the covering part according to the longitudinal axis (11) is closed. In some of these embodiments, this first end of the covering part (1) also comprises a third heating layer (5c) which heats the region of the feet of the user.

In some embodiments, the second end is open.

In some embodiments, the second end of the covering part comprises detachable closing and/or partial means of the second end. In some of these embodiments, such detachable closing and/or partial means are advantageously formed by a towel rail (12). The towel rail is formed for example by a strip of elastic textile fixed on the covering part such that the part between the two ends of the strip can be lifted so that a towel can be introduced. This towel recloses the second end of the covering part.

In some embodiments, the inner surface of the covering part is covered in material preventing the user from being in direct contact with the heating layer, such as for example textile.

In some embodiments, the surface of the support intended to be in contact with the user is covered in material which prevents the user from being in direct contact with the support and any heating layer it can contain. Such material can be textile and damping material can be associated with it for the comfort of the patient. As the user breathes in the device, it is generally preferred that this material is impermeable or is detachably arranged on the surface.

In some embodiments, the covering part (1) comprises at least two portions whereof a first portion (1*a*) and a second portion (1*b*). The first portion (1*a*) can retract on or in the second portion (1*b*) by sliding of the first portion (1*a*) according to the longitudinal axis (11) of the covering part (1). So, for example, when the first portion (1*a*) retracts on the second portion (1*b*), the first portion (1*a*) covers the second portion (1*b*). It is preferred in general that the portion which covers the other is that which corresponds to the end near which the user will have his head, in this case the first portion (1*a*) in illustrative and non-limiting figures.

In some embodiments, the sliding is permitted by a sliding system (7). According to a particular configuration, such a sliding system is obtained by runners such as drawer mechanisms. In another configuration such a sliding system can comprise at least one slider fixed on the first portion (1*a*) of the covering part (1). The slider(s) are fixed parallel to the longitudinal axis (11) of the covering part (1) at the end of the branches of the parabolic form. The slider(s) are each capable of moving in a slide fixed on the support (2) according to a longitudinal axis (11) of the covering part (1). In another configuration the slider (7*a*) is fixed to the outer surface of the second portion (1*b*) parallel to the longitudinal axis (11) of the covering part (1) at the ends of the branches of the parabolic form. The slides (7*b*) in which the sliders (7*a*) can slide are fixed on the inner surface of the first portion (1*a*) parallel to the longitudinal axis (11) of the covering part (1) at the ends of the parabolic form.

Figure 5:
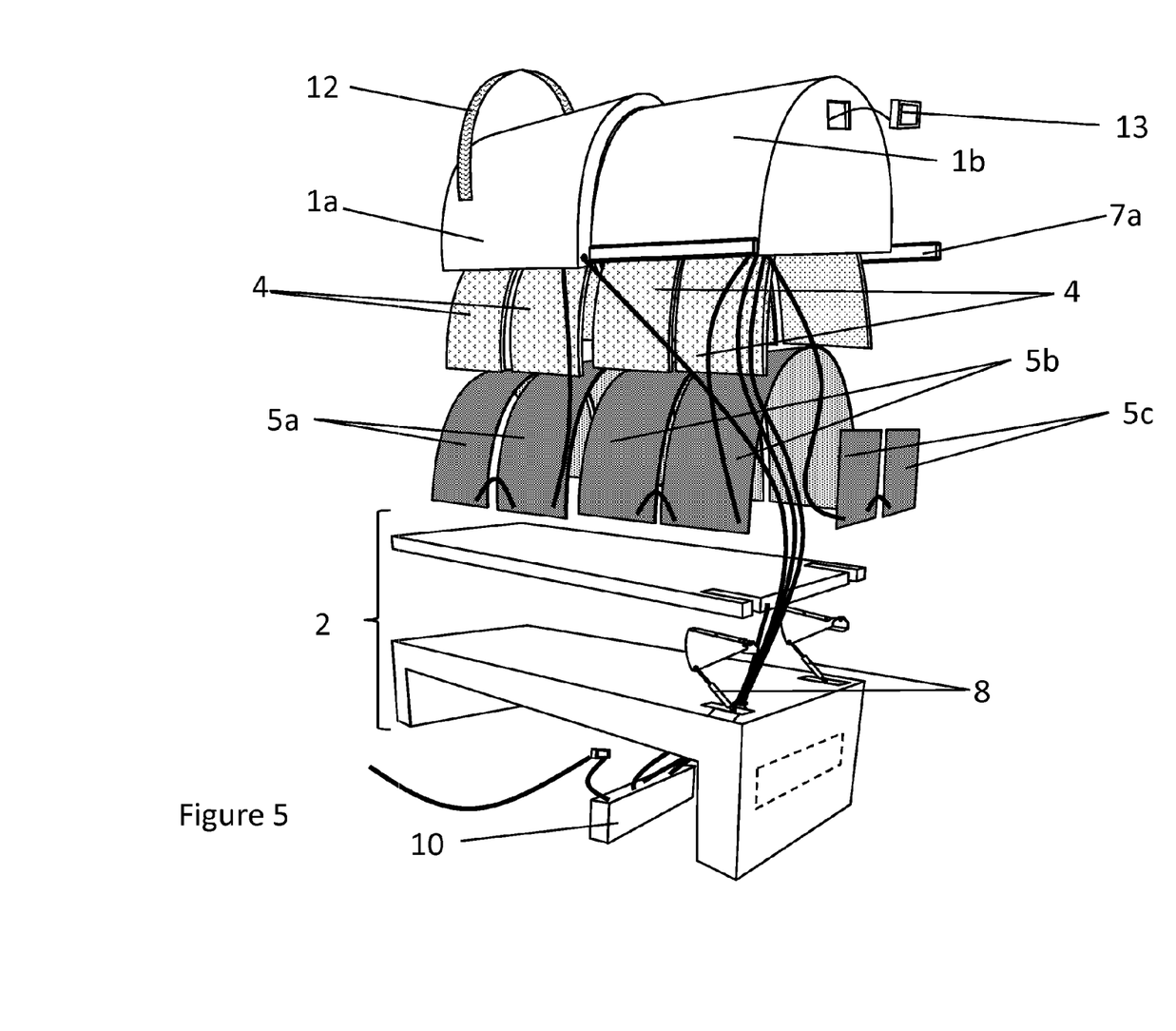
FIG. 5 illustrates an exploded view in perspective of the device.

In the illustrative and non-limiting configuration shown in FIG. 5, the covering part (1) comprises a first portion and a second portion. The first portion (1*a*) comprises an outer layer, two reflective layers (4) and two carbon plates (5*a*). The second portion (1*b*) also comprises an outer layer, two reflective layers (4) and two carbon plates (5*a*). The covering part is closed at an end by a rigid plate on which are fixed for example two carbon plates (5*c*). The support (2) also comprises at least one carbon plate.

In some embodiments, the carbon plates of the first portion are fed independently of the other plates.

In some embodiments, the carbon plates and/or the reflective layers are fixed against the outer layer by fastening means.

In some embodiments, the carbon plates of the second portion are fed independently of the other plates.

In some embodiments, the carbon plates of the support (2) are fed independently of the other plates.

In these embodiments where the plates are fed independently of each other, it is possible to modulate the infrared radiation according to the regions of the volume comprised between the covering part and the support (2). For example, the feed of the carbon plates of the first portion is regulated such that the infrared radiation produced has less intensity than the radiation produced by the carbon plates of the second portion.

In some embodiments, each portion and/or the support comprises several plates regulated independently of each other so as to provide even finer modulation of the infrared radiation, for example according to the areas to be treated in the case of phlebology. This arrangement further improves the reliability and the durability of the device.

Independently of the temperature control, the controller or even the form of the profile of the covering part, the irradiation device comprises a lifting system of the covering part. The first portion (1*a*) or the second portion (1*b*) of the covering part (1) is fixed on at least the lifting system of the covering part (1). The lifting system of the covering part (1) comprises at least one thrust jack (8) whereof an end is fixed on the support (2) or on the feet of the support (2) and the other end is fixed on the first or the second portion (1*b*) of the covering part (1) such that the jack (8) can exert thrust tending to lift an end of the covering part (1). The other end of the covering part (1) is fixed on the support (2) by means of a hinge allowing the longitudinal axis (11) of the covering part (1) to form a non-zero angle with the plane of the support (2). The thrust force of the jack(s) (8) is determined as a function of different positions of the first portion (1*a*). When the first portion (1*a*) does not cover the second portion (1*b*), the thrust force of the jack (8) is not sufficient to lift the non-fixed end of the covering part (1) whereof the longitudinal axis (11) remains parallel with the plane of the support (2). When the first portion (1*a*) covers the second portion (1*b*), the force of the jack (8) is sufficient to lift the fixed end of the covering part (1) whereof the longitudinal axis (11) forms a non-zero angle with the plane of the support (2). A stop element holds the covering part (1) when it is lifted by the jack(s) (8) to limit the angle formed by the longitudinal axis (11) of the covering part (1) and the plane of the support (2).

This arrangement has the advantage of easier opening of the device by the user himself not pushing on the first portion to make it slide and the first and the second portion lift up automatically under the action of the jack.

The invention therefore relates to any device comprising a support (2) and a covering part (1) arranged according to a longitudinal axis of the device. The covering part comprises a first portion slidably mounted on a second portion fixed by a pivoting axis on the support. The device comprises a jack mounted between the second portion and the support (2) or the feet of the support (2), the thrust force of the jack being adapted so that on the one hand the weight of the portions in deployed position prevents lifting of the two portions, and on the other hand when the portions are retracted at least partially, the force of the jack suffices to automatically lift the covering part.

The present description details different embodiments and configurations or variants in reference to figures and/or technical characteristics. Those skilled in the art will understand that the various technical characteristics of the various modes or configurations can be combined together to create other embodiments and configurations, unless specified otherwise or these technical characteristics are incompatible. Similarly, a technical characteristic of an embodiment or a configuration can be isolated from the other technical characteristics of this embodiment unless specified otherwise. In the present description, many specific details are provided by way of illustration and non-limiting so as to precisely detail the invention. Those skilled in the art, however, will understand that the invention can be executed in the absence of one or more of these specific details or with variants. On other occasions, some aspects are not detailed so as to prevent obscuring and weighing down the present description and those skilled in the art will understand various and varied means could be used and the invention is not limited to only those examples described.

It must be evident for those skilled in the art that the present invention allows embodiments in many other specific forms without departing from the field of application of the invention as claimed. Consequently, the present embodiments must be considered by way of illustration, but can be modified in the field defined by the scope of the appended claims, and the invention must not be limited to the details given hereinabove.

The invention claimed is:

1. An infrared irradiation device comprising:
   a support capable of receiving a user,
   a covering part capable of covering the user, the covering part comprising
      at least one heating layer capable of emitting infrared radiation in a determined range of wavelengths to at least one part of a volume located between an inner face of the at least one heating layer and the support,
   a power supply providing power necessary for emission of infrared radiation during an irradiation session, and
   at least one controller configured to regulate said at least one heating layer, said at least one controller comprising at least one programmer configured to
      determine parameters of the irradiation session, by defining variable time periods and variable frequencies applied during each of the variable time periods for each irradiation session, and
      cause the power supply to provide the power to said at least one heating layer through at least one contactor at said variable frequencies each of which is applied during each of said variable time periods to obtain different requested temperatures for the irradiation session at the defined variable time periods.

2. The device according to claim 1, wherein the at least one contactor is a synchronous static relay which delivers no current to said at least one heating layer beyond the time periods defined by the at least one programmer.

3. The device according to claim 1, wherein the programmer calculates the time at which the time periods must be delivered, and their period, as a function of the quantity of energy to be provided, and therefore of the requested temperature.

4. The device according to claim 1, wherein the programmer comprises a memory storing a plurality of predefined programs corresponding to various types of irradiation sessions and defining the period of the irradiation session and/or temperature(s) to be reached during the session.

5. The device according to claim 1, further comprising at least one probe or sensor, and the at least one programmer calculates the time periods as a function of temperature information originating from said probe or said sensor.

6. The device according to claim 5, wherein said at least one probe or sensor is at least one temperature probe allowing the at least one programmer to adjust the time periods as a function of the temperature obtained in the device.

7. The device according to claim 1, wherein the device is fitted with an electrical safety to protect the user from any problems in electrical circuits of the device.

8. The device according to claim 1, wherein the covering part further comprises a reflective layer of infrared radiation.

9. The device according to claim 8, wherein the reflective layer comprises at least one layer made of aluminum.

10. The device according to claim 1, wherein the support comprises a second heating layer capable of emitting radiation in at least one part of the volume between the inner face of the first heating layer and the support.

11. The device according to claim 10, wherein an end, according to a longitudinal axis, of the covering part comprises a third heating layer closing the covering part.

12. The device according to claim 1, wherein the covering part comprises at least two portions, a second portion of the covering part being capable of sliding relative to a first portion parallel to the longitudinal axis so as to retract in or on the first portion.

13. The device according to claim 12, wherein the device comprises power cabling and a guide to allow sliding of the two portions without jamming and/or damaging the power cabling.

14. The device according to claim 1, wherein the covering part comprises an outer layer protecting an interior of the covering part.

15. The device according to claim 14, wherein the outer layer is made of wood.

16. The device according to claim 1, wherein said at least one heating layer comprises at least one carbon plate.

17. The device according to claim 1, wherein the support is made of wood.

18. The device according to claim 1, wherein the inner face of the covering part is covered in textile.

19. The device according to claim 1, wherein
   the covering part comprises a first portion and a second portion and the irradiation device comprises a lifting system of the covering part, the first portion or the second portion of the covering part being fixed on at least the lifting system of the covering part, the lifting system of the covering part comprising at least one thrust jack having a first end fixed on the support and a second end fixed on the first portion or the second portion of the covering part such that the jack exerts thrust tending to lift an end of the covering part, the other end of the covering part being fixed on the support by a hinge allowing a longitudinal axis of the covering part to form a non-zero angle with the plane of the support.

20. The device according to claim 19, wherein the device includes power cabling of the at least one heating layer which passes near the hinge of the covering part to make for easier pivoting without jamming and/or damaging the power cabling.

* * * * *